(12) United States Patent
Reggiani et al.

(10) Patent No.: US 12,171,923 B2
(45) Date of Patent: *Dec. 24, 2024

(54) BLOOD PROCESSING UNIT WITH MODIFIED FLOW PATH

(71) Applicant: Sorin Group Italia S.r.l., Milan (IT)

(72) Inventors: Stefano Reggiani, Medolla (IT); Gianfranco Beniamino Fiore, Milan (IT); Alberto Redaelli, Milan (IT); Christian Baiotto, Mirandola (IT)

(73) Assignee: Sorin Group Italia S.r.l., Milan (IT)

( * ) Notice: Subject to any disclaimer, the term of this patent is extended or adjusted under 35 U.S.C. 154(b) by 569 days.

This patent is subject to a terminal disclaimer.

(21) Appl. No.: 17/496,330

(22) Filed: Oct. 7, 2021

(65) Prior Publication Data

US 2022/0023519 A1    Jan. 27, 2022

Related U.S. Application Data

(63) Continuation of application No. 16/203,483, filed on Nov. 28, 2018, now Pat. No. 11,160,912, which is a (Continued)

(30) Foreign Application Priority Data

Aug. 19, 2010   (EP) .................................... 10173436

(51) Int. Cl.
*A61M 1/16*   (2006.01)
*A61M 1/32*   (2006.01)
(Continued)

(52) U.S. Cl.
CPC ............ *A61M 1/1698* (2013.01); *A61M 1/32* (2013.01); *A61M 1/3627* (2013.01);
(Continued)

(58) Field of Classification Search
CPC .... A61M 1/1698; A61M 1/32; A61M 1/3627; A61M 1/3666; A61M 1/3667;
(Continued)

(56) References Cited

U.S. PATENT DOCUMENTS 3,339,341 A   9/1967   Maxwell et al.
3,957,648 A   5/1976   Roget et al.
(Continued)

FOREIGN PATENT DOCUMENTS

CN   1042082 A   5/1990
CN   1308549 A   8/2001
(Continued)

OTHER PUBLICATIONS

European Search Report issued in EP Application No. 10161451, dated Sep. 28, 2010. 5 pages.
(Continued)

*Primary Examiner* — Benjamin J Klein
(74) *Attorney, Agent, or Firm* — Seager, Tufte & Wickhem LLP

(57) ABSTRACT

A blood processing apparatus may include a heat exchanger and a gas exchanger. At least one of the heat exchanger and the gas exchanger may be configured to impart a radial component to blow flow through the heat exchanger and/or gas exchanger. The heat exchanger may be configured to cause blood flow to follow a spiral flow path.

20 Claims, 12 Drawing Sheets

Related U.S. Application Data continuation of application No. 15/215,527, filed on Jul. 20, 2016, now Pat. No. 10,159,777, which is a continuation of application No. 14/156,937, filed on Jan. 16, 2014, now Pat. No. 9,402,943, which is a continuation of application No. 13/753,638, filed on Jan. 30, 2013, now Pat. No. 8,652,406, which is a continuation of application No. 12/860,062, filed on Aug. 20, 2010, now Pat. No. 8,394,049.

(51) Int. Cl.
| | | |
|---|---|---|
| *A61M 1/36* | (2006.01) | |
| *B01D 63/02* | (2006.01) | |
| *F28D 7/10* | (2006.01) | |
| *F28D 7/16* | (2006.01) | |
| *F28D 21/00* | (2006.01) | |
| *F28F 13/06* | (2006.01) | |
| *F28F 21/06* | (2006.01) | |

(52) U.S. Cl.
CPC ........ *A61M 1/3666* (2013.01); *A61M 1/3667* (2014.02); *B01D 63/02* (2013.01); *F28D 7/103* (2013.01); *F28D 7/1623* (2013.01); *F28D 21/0015* (2013.01); *F28F 13/06* (2013.01); *F28F 21/06* (2013.01); *F28F 21/062* (2013.01); *A61M 1/3623* (2022.05); *A61M 2206/10* (2013.01); *A61M 2206/14* (2013.01); *A61M 2206/16* (2013.01); *A61M 2206/18* (2013.01); *A61M 2206/20* (2013.01); *B01D 2313/08* (2013.01); *B01D 2313/19* (2013.01); *B01D 2313/221* (2022.08); *B01D 2313/32* (2013.01); *F28D 2021/005* (2013.01); *F28F 2260/00* (2013.01); *Y10S 128/03* (2013.01); *Y10S 261/28* (2013.01)

(58) Field of Classification Search
CPC .......... A61M 2206/10; A61M 2206/14; A61M 2206/16; A61M 2206/18; A61M 2206/20; B01D 63/02; B01D 2313/08; B01D 2313/19; B01D 2313/32; B01D 2313/38; F28D 7/103; F28D 7/1623; F28D 21/0015; F28D 2021/005; F28F 13/06; F28F 21/06; F28F 21/062; F28F 2260/00; Y10S 128/03; Y10S 261/28
See application file for complete search history.

(56) References Cited

U.S. PATENT DOCUMENTS

| | | | |
|---|---|---|---|
| 4,038,190 A | 7/1977 | Baudet et al. | |
| 4,225,439 A | 9/1980 | Spranger | |
| 4,229,305 A | 10/1980 | Fecondini et al. | |
| 4,597,868 A | 7/1986 | Watanabe | |
| 4,639,353 A | 1/1987 | Takemura et al. | |
| 4,707,268 A | 11/1987 | Shah et al. | |
| 4,758,341 A | 7/1988 | Banner | |
| 4,902,476 A | 2/1990 | Gordon et al. | |
| 5,120,501 A | 6/1992 | Mathewson et al. | |
| 5,169,530 A | 12/1992 | Schucker et al. | |
| 5,192,439 A | 3/1993 | Roth et al. | |
| 5,192,499 A | 3/1993 | Sakai et al. | |
| 5,270,004 A | 12/1993 | Cosentino et al. | |
| 5,316,724 A | 5/1994 | Mathewson et al. | |
| 5,338,512 A | 8/1994 | Mathewson et al. | |
| 5,514,095 A | 5/1996 | Brightbill et al. | |
| 5,578,267 A | 11/1996 | Cosentino et al. | |
| 5,651,765 A | 7/1997 | Haworth et al. | |
| 5,674,452 A | 10/1997 | Carson et al. | |
| 5,733,398 A | 3/1998 | Carson et al. | |
| 5,762,868 A | 6/1998 | Leonard | |
| 5,762,869 A | 6/1998 | White et al. | |
| 5,817,278 A | 10/1998 | Fini et al. | |
| 5,817,279 A | 10/1998 | Eilers et al. | |
| 5,830,370 A | 11/1998 | Maloney, Jr. et al. | |
| RE36,774 E | 7/2000 | Cosentino et al. | |
| 6,105,664 A | 8/2000 | Gillbrand et al. | |
| 6,113,782 A | 9/2000 | Leonard | |
| 6,241,945 B1 | 6/2001 | Owen | |
| 6,454,999 B1 | 9/2002 | Farhangnia et al. | |
| 6,459,937 B1 | 10/2002 | Morgan et al. | |
| 6,755,894 B2 | 6/2004 | Bikson et al. | |
| 6,960,322 B2 | 11/2005 | Stringer et al. | |
| 7,431,754 B2 | 10/2008 | Ogihara et al. | |
| 7,947,113 B2 | 5/2011 | Ogihara et al. | |
| 7,981,121 B2 | 7/2011 | Stegfeldt et al. | |
| 8,142,546 B2 | 3/2012 | Ogihara et al. | |
| 8,318,092 B2 | 11/2012 | Reggiani et al. | |
| 8,388,566 B2 | 3/2013 | Reggiani et al. | |
| 8,394,049 B2 * | 3/2013 | Reggiani ................. | F28F 13/06 604/46 |
| 8,425,838 B2 | 4/2013 | Mizoguchi et al. | |
| 8,652,406 B2 * | 2/2014 | Reggiani ............... | F28D 7/1623 422/46 |
| 8,685,319 B2 | 4/2014 | Olson et al. | |
| 8,795,220 B2 * | 8/2014 | Reggiani ............... | F28F 21/062 604/4.01 |
| 8,865,067 B2 | 10/2014 | Olson et al. | |
| 8,911,666 B2 | 12/2014 | Mizoguchi et al. | |
| 8,980,176 B2 | 3/2015 | Reggiani et al. | |
| 9,162,022 B2 | 10/2015 | Reggiani et al. | |
| 9,402,943 B2 * | 8/2016 | Reggiani ............... | F28F 21/062 |
| 10,098,994 B2 | 10/2018 | Silvestri et al. | |
| 10,159,777 B2 * | 12/2018 | Reggiani ............ | A61M 1/3627 |
| 10,369,262 B2 | 8/2019 | Reggiani | |
| 2001/0033813 A1 | 10/2001 | Filho et al. | |
| 2002/0039543 A1 | 4/2002 | Ikeda et al. | |
| 2002/0049401 A1 | 4/2002 | Ghelli et al. | |
| 2003/0080047 A1 | 5/2003 | Watkins et al. | |
| 2003/0111414 A1 | 6/2003 | Baurmeister et al. | |
| 2003/0175149 A1 | 9/2003 | Searles et al. | |
| 2004/0149645 A1 | 8/2004 | Sunohara et al. | |
| 2004/0175292 A1 | 9/2004 | Ghelli et al. | |
| 2004/0251011 A1 | 12/2004 | Kudo | |
| 2006/0016743 A1 | 1/2006 | Ogihara et al. | |
| 2007/0009378 A1 | 1/2007 | Blicke et al. | |
| 2007/0107884 A1 | 5/2007 | Sirkar et al. | |
| 2007/0166190 A1 | 7/2007 | Ogihara et al. | |
| 2007/0231203 A1 | 10/2007 | Mizoguchi et al. | |
| 2008/0234623 A1 | 9/2008 | Strauss et al. | |
| 2009/0018629 A1 | 1/2009 | Yoshida et al. | |
| 2010/0106072 A1 | 4/2010 | Kashefi-Khorasani et al. | |
| 2010/0269342 A1 | 10/2010 | Carpenter et al. | |
| 2010/0272606 A1 | 10/2010 | Carpenter et al. | |
| 2010/0272607 A1 * | 10/2010 | Carpenter ........... | A61M 1/3623 422/46 |
| 2011/0268608 A1 | 11/2011 | Reggiani et al. | |
| 2011/0268609 A1 | 11/2011 | Reggiani et al. | |
| 2012/0046594 A1 | 2/2012 | Reggiani et al. | |
| 2012/0121463 A1 | 5/2012 | Reggiani et al. | |
| 2012/0294761 A1 | 11/2012 | Reggiani et al. | |
| 2013/0142695 A1 | 6/2013 | Reggiani et al. | |
| 2013/0142696 A1 | 6/2013 | Reggiani et al. | |
| 2014/0030146 A1 | 1/2014 | Takeuchi | |
| 2014/0154137 A1 | 6/2014 | Kashefi Khorasani | |
| 2014/0227133 A1 | 8/2014 | Reggiani et al. | |
| 2015/0068670 A1 | 3/2015 | Mizoguchi et al. | |
| 2016/0325036 A1 | 11/2016 | Silvestri et al. | |
| 2016/0354529 A1 | 12/2016 | Reggiani et al. | |
| 2017/0072123 A1 | 3/2017 | Reggiani | |
| 2017/0319767 A1 | 11/2017 | Zaniboni et al. | |
| 2018/0133388 A1 | 5/2018 | Mazzoli et al. | |
| 2019/0290821 A1 | 9/2019 | Reggiano | |

FOREIGN PATENT DOCUMENTS

| | | |
|---|---|---|
| CN | 2511309 Y | 9/2002 |
| CN | 2772515 Y | 4/2006 |
| CN | 1907508 A | 2/2007 |

(56) References Cited

FOREIGN PATENT DOCUMENTS

| | | |
|---|---|---|
| CN | 1914474 A | 2/2007 |
| CN | 201510571 U | 6/2010 |
| CN | 101837151 A | 9/2010 |
| CN | 201978219 U | 9/2011 |
| CN | 103180032 A | 6/2013 |
| CN | 103328019 A | 9/2013 |
| CN | 103547298 A | 1/2014 |
| CN | 106029118 A | 10/2016 |
| DE | 19782098 T1 | 11/1999 |
| DE | 102007010112 A1 | 9/2008 |
| DE | 102010027973 A1 | 10/2011 |
| EP | 0170210 A2 | 2/1986 |
| EP | 0312125 A1 | 4/1989 |
| EP | 0582959 A1 | 2/1994 |
| EP | 0895786 A1 | 2/1999 |
| EP | 1108462 A2 | 6/2001 |
| EP | 1180374 A1 | 2/2002 |
| EP | 0876170 B1 | 10/2003 |
| EP | 1371381 A1 | 12/2003 |
| EP | 1618906 A1 | 1/2006 |
| EP | 1834656 A1 | 9/2007 |
| EP | 2420262 A1 | 2/2012 |
| EP | 2524712 A1 | 11/2012 |
| EP | 2537543 A1 | 12/2012 |
| EP | 2692370 A1 | 2/2014 |
| JP | S445526 Y1 | 2/1969 |
| JP | S52126681 A | 10/1977 |
| JP | S59147603 A | 8/1984 |
| JP | S60053156 A | 3/1985 |
| JP | S61078407 A | 4/1986 |
| JP | S63139562 A | 6/1988 |
| JP | S63283709 A | 11/1988 |
| JP | H03169329 A | 7/1991 |
| JP | H042067 B2 | 1/1992 |
| JP | H0439862 B2 | 6/1992 |
| JP | H05-177117 A | 7/1993 |
| JP | H07-088178 A | 4/1995 |
| JP | H08-168525 A | 7/1996 |
| JP | H115081476 A | 7/1999 |
| JP | 9947189 A1 | 9/1999 |
| JP | 2000-501954 A | 2/2000 |
| JP | 20000-093510 A | 4/2000 |
| JP | 3228518 B2 | 11/2001 |
| JP | 2002-506692 A | 3/2002 |
| JP | 3284568 B2 | 5/2002 |
| JP | 2002306592 A | 10/2002 |
| JP | 2003520617 A | 7/2003 |
| JP | 2003525736 A | 9/2003 |
| JP | 2004216143 A | 8/2004 |
| JP | 2006034466 A | 2/2006 |
| JP | 2007190218 A | 8/2007 |
| JP | 2007244880 A | 9/2007 |
| JP | 3992377 B2 | 10/2007 |
| JP | 2007260151 A | 10/2007 |
| JP | 2007328114 A | 12/2007 |
| JP | 2009093659 A | 4/2009 |
| JP | 2011047269 A | 3/2011 |
| JP | 5020111 B2 | 9/2012 |
| JP | 2012239885 A | 12/2012 |
| JP | 2013063121 A | 4/2013 |
| JP | 2015144857 A | 8/2015 |
| JP | 2017510340 A | 4/2017 |
| WO | 9716213 A2 | 5/1997 |
| WO | 9719714 A1 | 6/1997 |
| WO | 9733636 A1 | 9/1997 |
| WO | 9822161 A1 | 5/1998 |
| WO | 9958171 A2 | 11/1999 |
| WO | 0006357 A1 | 2/2000 |
| WO | 0166237 A1 | 9/2001 |
| WO | 2010124087 A1 | 10/2010 |
| WO | 2012133372 A1 | 1/2012 |
| WO | 2012066439 A1 | 5/2012 |
| WO | 2015104725 A1 | 7/2015 |
| WO | 2015107486 A2 | 7/2015 |
| WO | 2015128886 A1 | 9/2015 |

OTHER PUBLICATIONS

European Search Report in EP Application No. 10173436, dated Feb. 14, 2011, 7 pages.
European Search Report issued in EP Application No. 10186550, dated Jan. 27, 2011, 7 pages.
European Search Report issued in EP Application No. 10191140, dated Nov. 30, 2011, 8 pages.
European Search Report issued in EP Application No. 12187501, dated Nov. 20, 2013, 6 pages.
European Search Report issued in EP Application No. 13161841, dated Jun. 11, 2013, 6 pages.
International Search Report and Written Opinion issued in PCT/IB2012/052424, dated Oct. 24, 2012, 17 pages.
International Search Report and Written Opinion issued in PCT/IB2014/065987, dated Jul. 6, 2015, 10 pages.
International Search Report and Written Opinion issued in PCT/IB2015/053493, dated Jan. 18, 2016, 13 pages.
Italian Search Report issued in IT Application No. It MO20140010, dated Sep. 23, 2014, 7 pages.
International Search Report and Written Opinion issued in PCT/IT2014/000058, dated Dec. 8, 2014, 14 pages.
International Search Report and Written Opinion received for PCT Patent Application No. PCT/IT2014/000005, dated Sep. 26, 2014, 8 pages.
International Search Report issued in PCT/IB2011/054725, dated Feb. 9, 2021, 12 pages.

\* cited by examiner

BLOOD PROCESSING UNIT WITH MODIFIED FLOW PATH

CROSS-REFERENCE TO RELATED APPLICATION

This application is a continuation of U.S. application Ser. No. 16/203,483, filed Nov. 28, 2018, which is a continuation of U.S. application Ser. No. 15/215,527, filed Jul. 20, 2016, now U.S. Pat. No. 10,159,777, which is a continuation of U.S. application Ser. No. 14/156,937, filed Jan. 16, 2014, now U.S. Pat. No. 9,402,943, which is a continuation of U.S. application Ser. No. 13/753,638, filed Jan. 30, 2013, now U.S. Pat. No. 8,652,406, which is a continuation of U.S. application Ser. No. 12/860,062, filed Aug. 20, 2010, now U.S. Pat. No. 8,394,049, which claims priority to European Application No. EP10173436.6, filed Aug. 19, 2010, under 35 U.S.C. § 119, all of which are herein incorporated by reference in their entireties.

TECHNICAL FIELD

The disclosure pertains generally to blood processing units used in blood perfusion systems.

BACKGROUND

Blood perfusion entails encouraging blood through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral artery, or other artery.

SUMMARY

Example 1 is a blood processing apparatus including a housing having a blood inlet and a blood outlet, the blood inlet extending into an interior of the housing. A heat exchanger core is arranged coaxially within the housing, the heat exchanger core including an outer surface configured to impart a radial blood flow component and a core aperture in fluid communication with the blood inlet and configured to permit blood to pass from the blood inlet to an exterior of the heat exchanger core. Heat exchanger hollow fibers are disposed about the heat exchanger core such that a heat exchanger fluid may flow through the heat exchanger hollow fibers and blood passing from the core aperture may flow across the heat exchanger hollow fibers. A cylindrical shell extends coaxially about the heat exchanger core, the cylindrical shell including an annular shell aperture disposed near an end of the cylindrical shell opposite to an end near which the core aperture is located, the annular shell aperture configured to permit blood to pass to an exterior of the cylindrical shell. Gas exchanger hollow fibers are disposed about the cylindrical shell such that gases may flow through the gas exchange hollow fibers and blood passing from the annular shell aperture may flow across the gas exchanger hollow fibers.

In Example 2, the blood processing apparatus of Example 1 in which the outer surface of the heat exchanger core includes one or more radially disposed core ribs configured to impart a radial component to blood flow across the heat exchanger hollow fibers.

In Example 3, the blood processing apparatus of Example 1 or Example 2 in which the cylindrical shell includes an inner surface upon which one or more radially disposed shell ribs are disposed, the one or more radially disposed shell ribs configured to impart a radial component to blood flow trajectory across the heat exchanger hollow fibers.

In Example 4, the blood processing apparatus of any of Examples 1-3 in which the heat exchanger core includes a conical deflection surface that is disposed between the blood inlet and the core aperture, the conical deflection surface imparting a radial component to blood flow trajectory leaving the core aperture.

In Example 5, the blood processing apparatus of any of Examples 1-4 in which the housing includes an inner surface upon which one or more radially disposed housing ribs are disposed, the one or more radially disposed housing ribs configured to impart a radial component to blood flow trajectory across the gas exchanger hollow fibers.

In Example 6, the blood processing apparatus of Example 1 in which the core aperture includes a pair of core apertures disposed about 180 degrees apart, and the annular shell aperture includes a pair of shell apertures that are disposed about 180 degrees apart and radially offset from the pair of core apertures in order to alter blood flow trajectory of the blood flowing across the heat exchanger hollow fibers.

In Example 7, the blood processing apparatus of any of Examples 1-6, further including a first end cap secured to the housing, the blood inlet being integrally formed with the first end cap.

In Example 8, the blood processing apparatus of Example 7, further including a gas inlet integrally formed with the first end cap, the gas inlet in fluid communication with an interior of the gas exchanger hollow fibers.

In Example 9, the blood processing apparatus of any of Examples 1-8, further including a second end cap secured to the housing, the second end cap including a heat exchanger fluid inlet integrally formed with the second end cap and a heat exchanger fluid outlet integrally formed with the second end cap, the heat exchanger fluid inlet and outlet each in fluid communication with an interior of the heat exchanger hollow fibers.

In Example 10, the blood processing apparatus of Example 9, further including a gas outlet integrally formed with the second end cap, the gas outlet in fluid communication with an interior of the gas exchanger hollow fibers.

Example 11 is blood processing apparatus including a housing having a blood inlet and a blood outlet, the blood inlet extending into an interior of the housing. A heat exchanger core is disposed within the housing and in operative communication with the blood inlet, the heat exchanger core including an exterior surface and a core aperture in fluid communication with the blood inlet and configured to permit blood to pass from the blood inlet to an exterior of the heat exchanger core. Heat exchanger hollow fibers are disposed about the heat exchanger core such that a heat exchanger fluid may flow through the heat exchanger hollow fibers and blood passing from the core aperture may flow across the heat exchanger hollow fibers. The heat exchanger core includes one or more radially disposed ribs configured to impart a radial component to blood flow across the heat exchanger hollow fibers. A cylindrical shell extends coaxially about the heat exchanger core, the cylindrical shell including an annular shell aperture disposed near an end of the cylindrical shell opposite to an end near which the core aperture is located, the annular shell aperture configured to permit blood to pass to an exterior of the cylindrical shell. Gas exchanger hollow fibers are disposed about the cylindrical shell such that gases may flow through the gas exchange hollow fibers and blood passing from the annular shell aperture may flow across the gas exchanger hollow fibers. One or more ribs are radially disposed on an outer surface of the cylindrical shell, the one or more radially disposed ribs configured to impart a radial component to blood flow across the gas exchanger hollow fibers.

In Example 12, the blood processing apparatus of Example 11 in which the cylindrical shell includes an inner surface upon which one or more radially disposed shell ribs are disposed, the one or more radially disposed shell ribs configured to impart a radial component to blood flow trajectory across the heat exchanger hollow fibers.

In Example 13, the blood processing apparatus of Example 11 or Example 12 in which the heat exchanger core includes a conical deflection surface disposed between the blood inlet and the core aperture, the conical deflection surface imparting a radial component to blood flow trajectory leaving the core aperture.

In Example 14, the blood processing apparatus of any of Examples 11-13 in which the housing includes an inner surface upon which one or more radially disposed housing ribs are disposed, the one or more radially disposed housing ribs configured to impart a radial component to blood flow trajectory across the gas exchanger hollow fibers.

In Example 15, the blood processing apparatus of any of Examples 11-14, further including one or more radially disposed ribs that are disposed on an inner surface of the cylindrical shell and configured to impart a radial component to blood flow trajectory across the heat exchanger hollow fibers.

In Example 16, the blood processing apparatus of any of Examples 11-15, further including one or more radially disposed ribs that are disposed on an inner surface of the housing and configured to impart a radial component to blood flow trajectory across the gas exchanger hollow fibers.

Example 17 is a blood processing apparatus that includes a housing having a blood inlet extending into an interior of the housing and a blood outlet. A heat exchanger core extends coaxially within the housing and is axially aligned with the blood inlet. The heat exchanger core includes a pair of core apertures that are disposed about 180 degrees apart and that are configured to permit blood to pass from the blood inlet to an exterior of the heat exchanger core. Heat exchanger hollow fibers are disposed about the heat exchanger core such that a heat exchanger fluid may flow through the heat exchanger hollow fibers and blood passing from the core aperture may flow across the heat exchanger hollow fibers. A cylindrical shell extends coaxially about the heat exchanger core and includes a pair of shell apertures that are disposed about 180 degrees apart and that are radially offset from the pair of core apertures in order to cause a spiral blood flow through the heat exchanger hollow fibers. The blood processing apparatus includes gas exchanger hollow fibers that are disposed about the cylindrical shell such that gases may flow through the gas exchange hollow fibers and blood passing from the annular shell aperture may flow across the gas exchanger hollow fibers.

In Example 18, the blood processing apparatus of Example 17 in which the pair of shell apertures are disposed near an end of the cylindrical shell opposite to an end near where the pair of core apertures is located.

In Example 19, the blood processing apparatus of Examples 17 or 18 wherein at least one of the heat exchanger hollow fibers and the gas exchanger hollow fibers are made from a polymer material.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

The disclosure pertains to a blood processing apparatus that, according to various exemplary embodiments, includes one or more of a heat exchanger and a gas exchanger (also commonly referred to as an oxygenator). In some embodiments, the term oxygenator may be used to refer to an integrated structure that combines a heat exchanger and a gas exchanger in a unitary device. In various embodiments, for example, the heat exchanger and gas exchanger are disposed in a concentric fashion with one component located inside of the other component. According to other embodiments, the heat exchanger and gas exchanger are structurally distinct structures operable coupled to each other. In some embodiments, an oxygenator may be used in an extracorporeal blood circuit. An extracorporeal blood circuit, such as may be used in a bypass procedure, may include several different elements such as a heart-lung machine, a blood reservoir, as well as an oxygenator.

Figure 1:
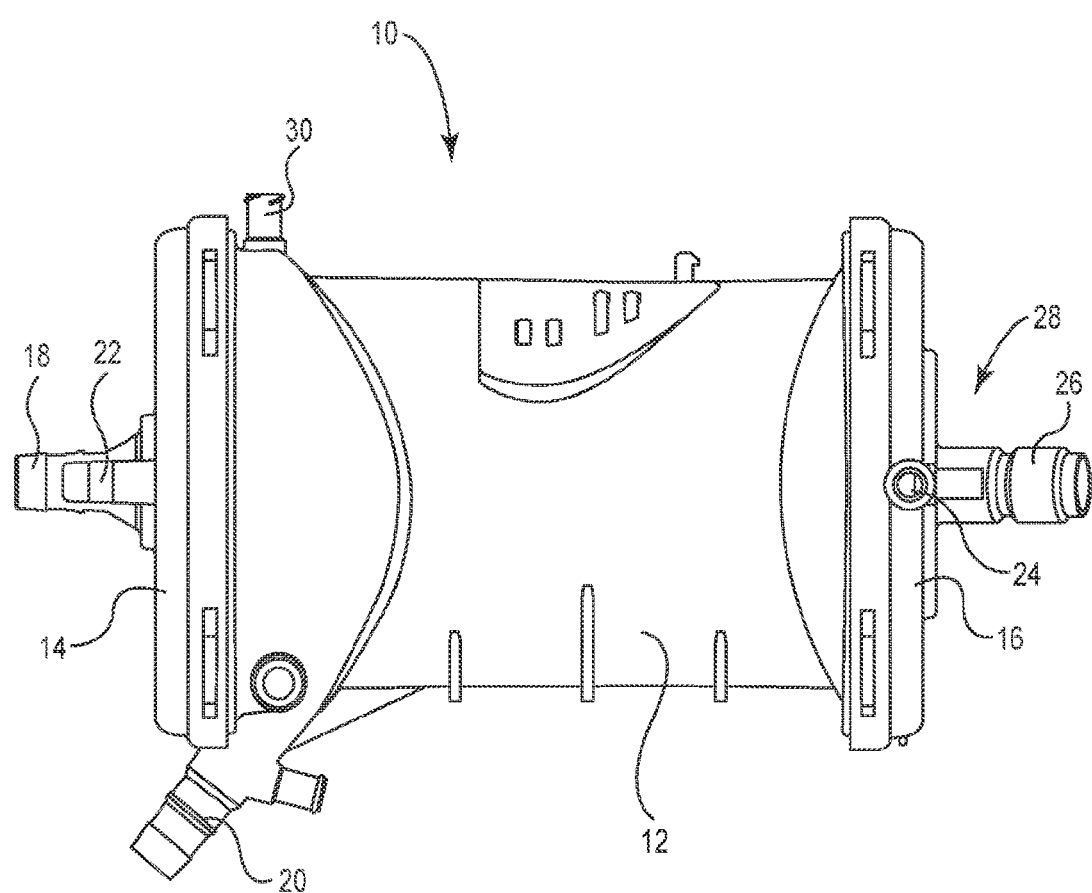
FIG. 1 is a schematic illustration of a blood processing apparatus in accordance with an embodiment of the invention.

FIG. 1 is a schematic illustration of a blood processing apparatus or oxygenator 10. While the internal components are not visible in this illustration, the oxygenator 10 may include one or more of a heat exchanger and a gas exchanger. According to some embodiments, the heat exchanger and the gas exchanger are integrated into a single structure that forms an oxygenator housing. The oxygenator 10 includes a housing 12, a first end cap 14 that is secured to the housing 12 and a second end cap 16 that is secured to the housing 12. In some embodiments, the housing 12 may include other structure that enables attachment of the housing 12 to other devices. While the housing 12 is illustrated as largely cylindrical in shape, in some embodiments, the housing 12 may have a rectangular or other parallelogram cross-sectional shape. Each of the heat exchanger and the gas exchanger may have generally the same sectional shape or each may have a different sectional shape. In some embodiments, the heat exchanger may be inside the gas exchanger while in other embodiments the gas exchanger may be located within the heat exchanger. In some embodiments, the heat exchanger and the gas exchanger may be concentric.

In some embodiments, a blood inlet 18 extends into the housing 12 and a blood outlet 20 exits the housing 12. As noted, in some embodiments the blood processing apparatus 10 includes a gas exchanger and thus may include a gas inlet 22 and a gas outlet 24. In some embodiments, the blood processing apparatus 10 includes a heat exchanger and thus may include a heat exchanger fluid inlet 26 and a heat exchanger fluid outlet 28 that is behind (in the illustrated orientation) the heating fluid inlet 26. In some embodiments, the heat exchanger fluid inlet 26 may be disposed at one end of the housing 12 while the heat exchanger fluid outlet 28 may be disposed at an opposite end of the housing 12. In some embodiments, the blood processing apparatus 10 may include a purge port 30 that may be used for purging air bubbles from the interior of the blood processing apparatus 10.

The positions of the inlets, outlets and purge port are merely illustrative, as other arrangements and configurations are contemplated. The purge port may include a valve or a threaded cap. The purge port operates to permit gases (e.g., air bubbles) that exit the blood to be vented or aspirated and removed from the blood processing apparatus 10.

Figure 2:
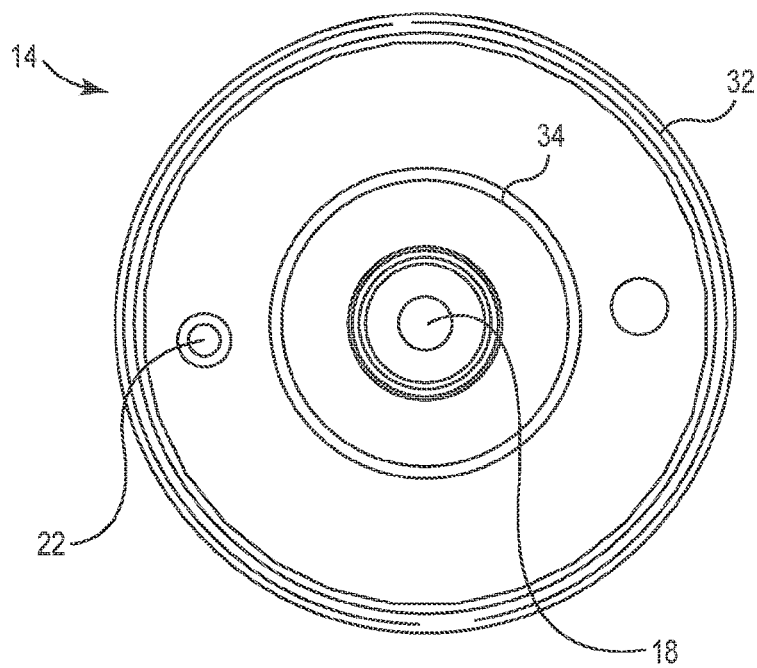
FIG. 2 is an illustration of a first end cap in accordance with an embodiment of the invention.
Figure 3:
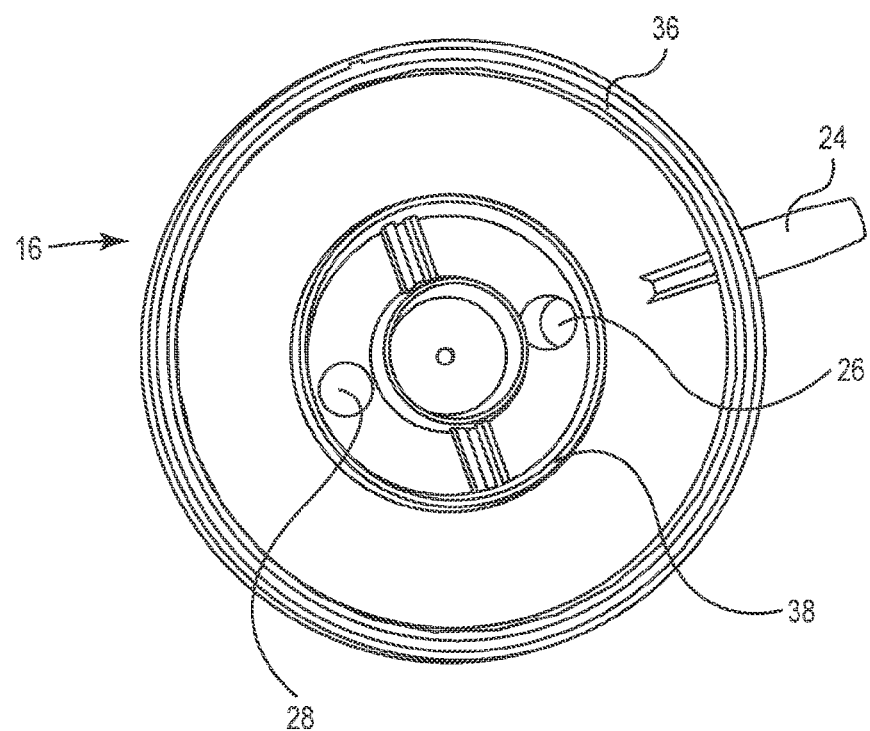
FIG. 3 is an illustration of a second end cap in accordance with an embodiment of the invention.

FIGS. 2 and 3 illustrate the first end cap 14 and the second end cap 16, respectively. The first end cap 14 and the second end cap 16 are each configured to be secured to the housing 12. In some embodiments, the first end cap 14 and/or the second end cap 16 may be adhesively secured in place. In some embodiments, the first end cap 14 and/or the second end cap 16 may be snap-fitted into place or even threaded onto their respective ends of the housing 12.

In some embodiments, as shown in FIG. 2, the blood inlet 18 and/or the gas inlet 22 may be integrally formed with the first end cap 14. For example, in some cases the first end cap 14 may be injection molded with the blood inlet 18 and/or the gas inlet 22 formed as part of the injection molded part.

In some embodiments, the first end cap 14 may be formed having apertures to which the blood inlet 18 and/or the gas inlet 22 may be attached. The first end cap 14 includes an annular ring 32 that is disposed about a periphery of the first end cap 14 and that serves, in some embodiments, as an attachment point for securing the first end cap 14 to the housing 12. In some embodiments, the first end cap 14 also includes an annular ring 34 that, as will be described subsequently, locates portions of the heat exchanger.

In some embodiments, as shown in FIG. 3, the heat exchanger fluid inlet 26 and/or the heat exchanger fluid outlet 28 may be integrally formed with the second end cap 16. For example, in some cases the second end cap 16 may be injection molded with the heat exchanger fluid inlet 26 and/or the heat exchanger fluid outlet 28 formed as part of the injection molded part. Similarly, in some embodiments, the second end cap 16 may be injected molded with the gas outlet 24 formed as part of the injection molded part. However, in some embodiments, the second end cap 16 may be formed having apertures to which one or more of the heat exchanger fluid inlet 26, the heat exchanger fluid outlet 28 and/or the gas outlet 24 may be attached. The second end cap 16 includes an annular ring 36 that is disposed about a periphery of the second end cap 16 and that serves, in some embodiments, as an attachment point for securing the second end cap 16 to the housing 12. In some embodiments, the second end cap 16 also includes an annular ring 38 that, as will be described subsequently, locates portions of the heat exchanger.

In some embodiments, one of the heat exchanger fluid inlet 26 and the heat exchanger fluid outlet 28 may be located in the first end cap 14 while the other of the heat exchanger fluid inlet 26 and the heat exchanger fluid outlet 28 may be located in the second end cap 16. In some embodiments, the heat exchanger fluid inlet 26 and outlet 28 may be located in the first end cap 14. In some embodiments, the heat exchanger fluid inlet 26 and outlet 28 may be located in the second end cap 16.

Figure 4:
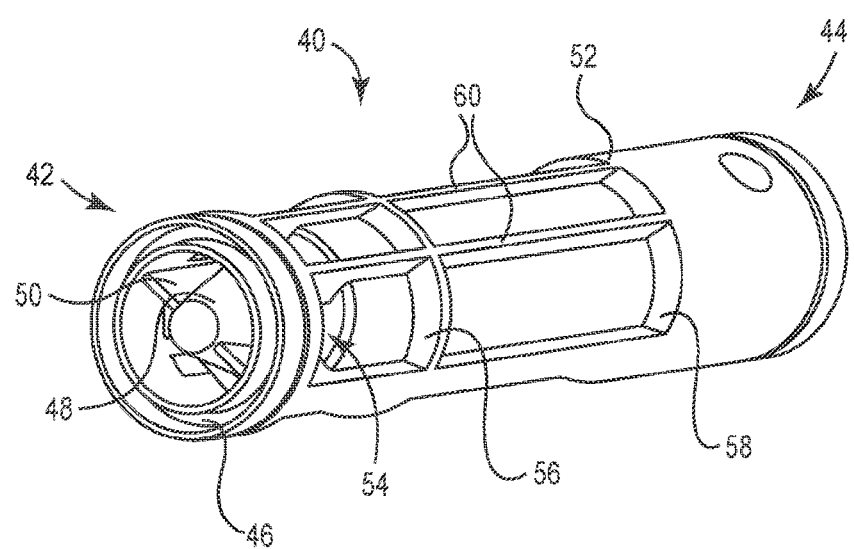
FIG. 4 is a perspective illustration of a heat exchanger core in accordance with an embodiment of the invention.

FIG. 4 is a perspective illustration of a heat exchanger core 40 having a first end 42 and a second end 44. In some embodiments, as will be illustrated with respect to subsequent drawings, the heat exchanger core 40 may be disposed within the blood processing apparatus 10 such that the first end 42 is near the first end cap 14 while the second end 44 is near the second end cap 16. The heat exchanger core 40 includes an annular portion 46 that, in some embodiments, helps to locate the first end 42 relative to the first end cap 14. Similarly, the second end 44 may be configured to help locate the second end 44 relative to the second end cap 16.

The heat exchanger core 40 includes a conical deflection surface 48 upon which incoming blood from the blood inlet 18 impinges. The conical deflection surface 48 deflects the blood in a radial direction. In some embodiments, the conical deflection surface 48 may include a divider 50 that assists in directing blood in particular directions. The heat exchanger core 40 includes an outer surface 52. A core aperture 54 is formed within the outer surface 52 such that blood impinging on the conical deflection surface 48 is deflected radially outwardly through the core aperture 54. In some embodiments, the heat exchanger core 40 may have one, two, three, four or any desired number of core apertures 54 spaced radially about the heat exchanger core 40.

In some embodiments, as illustrated, the heat exchanger core 40 includes a first radially disposed core rib 56 and a second radially disposed core rib 58. In some embodiments, the core ribs (or projections) 56 and 58 deflect blood away from the outer surface 52 in a radially-outward direction.

The core ribs 56 and 58 are designed to impart a radial component to blood flow trajectory. While two core ribs 56 and 58 are illustrated, in some cases the heat exchanger core 40 may include a greater number of core ribs. In some embodiments, the heat exchanger core 40 may also include longitudinally-extending ribs 60 that may serve to promote longitudinal flow paths down the outside of the heat exchanger core 40. According to various embodiments, the ribs 56 and 58 extend circumferentially around or substantially around the outer surface of the heat exchanger core 40.

Figure 5A:
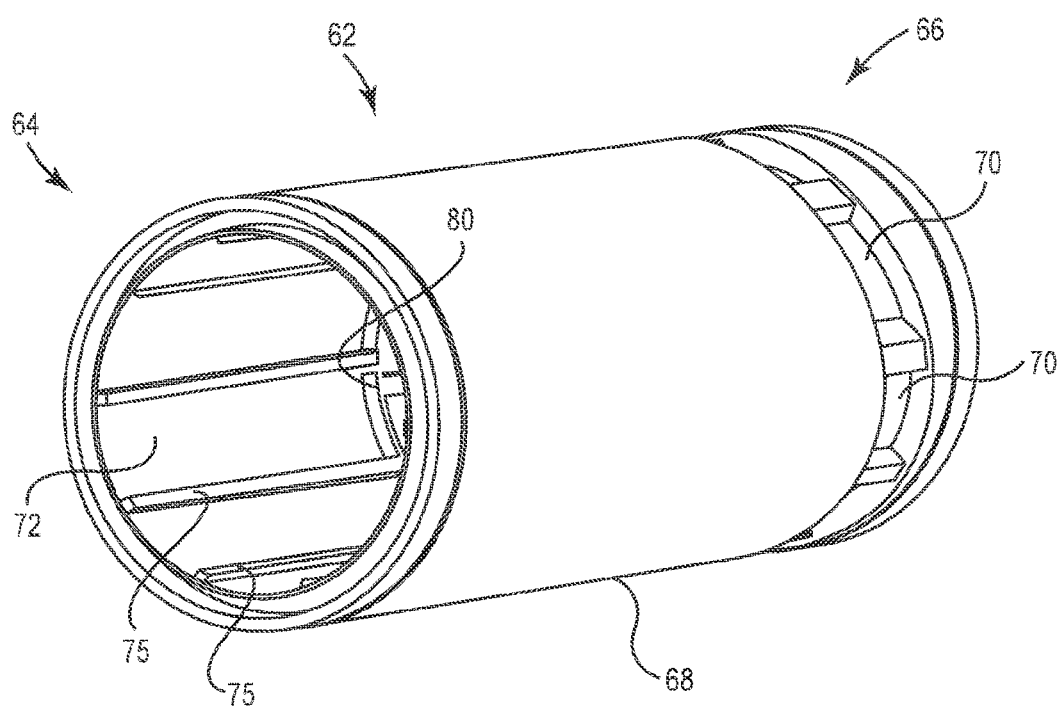
FIG. 5A is a perspective view of a cylindrical shell forming a barrier between a heat exchanger and a gas exchanger in accordance with an embodiment of the invention.
Figure 5B:
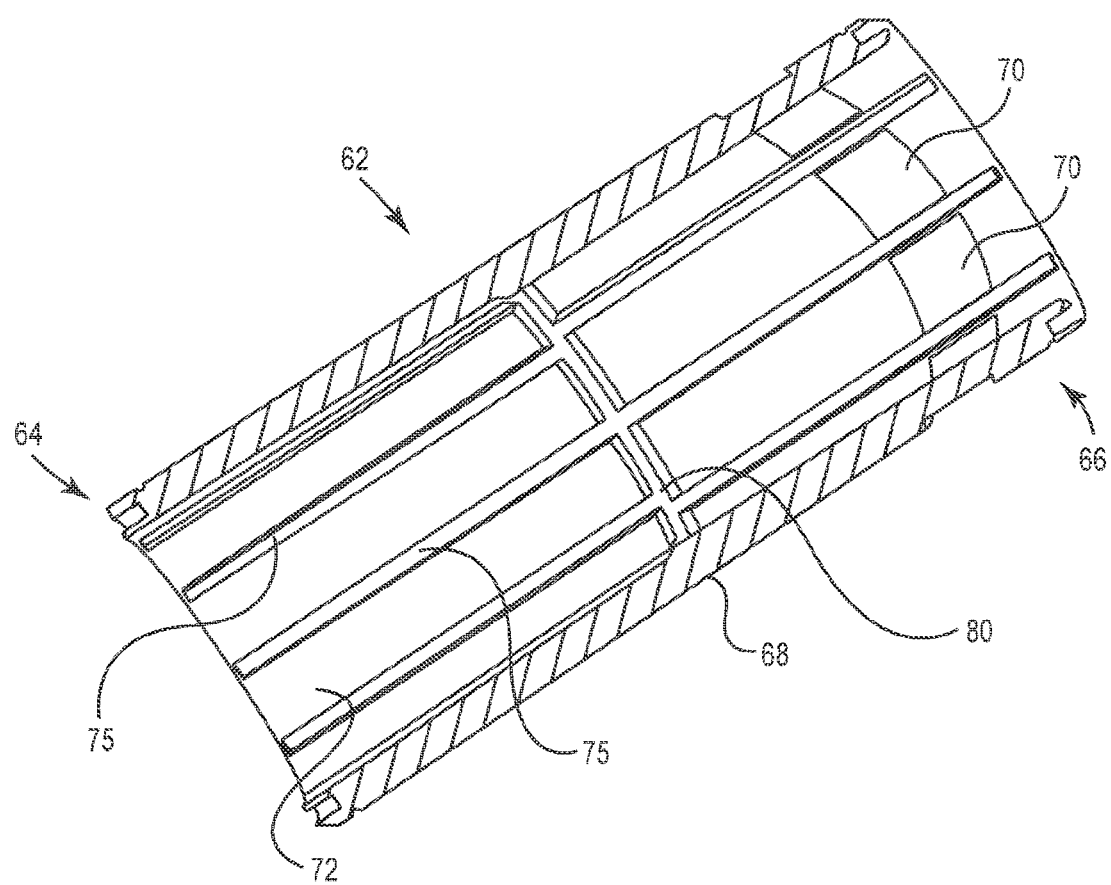
FIG. 5B is a cross-sectional view of the cylindrical shell of FIG. 5A.
Figure 6:
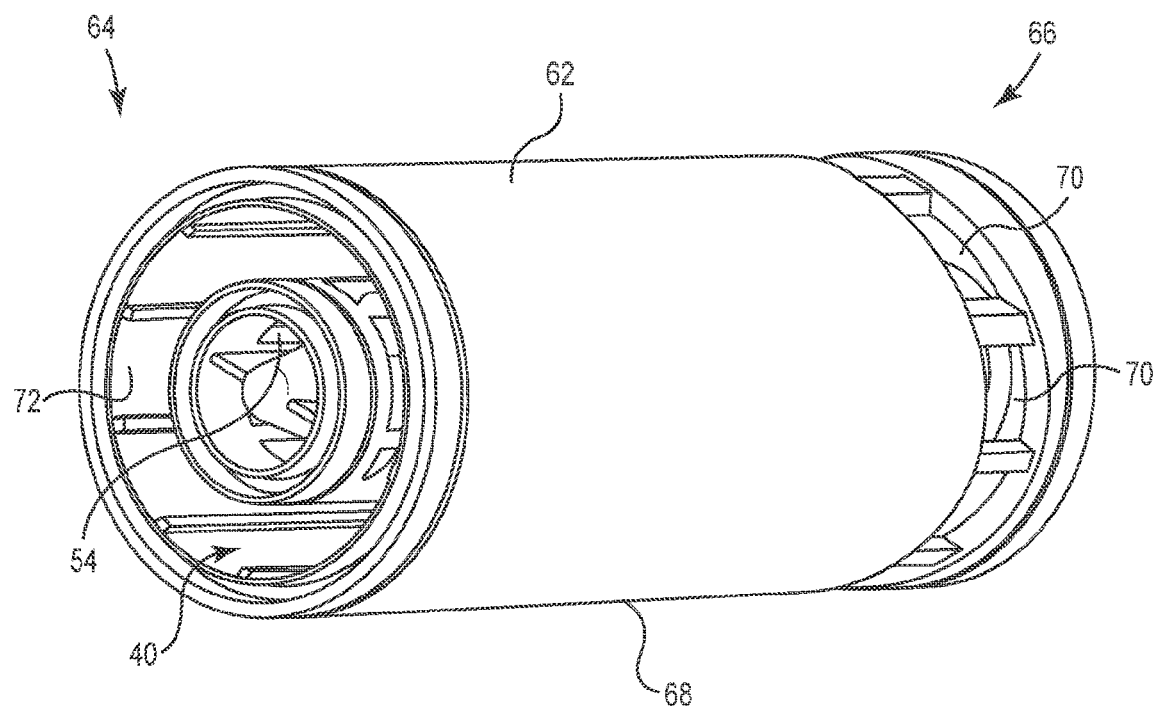
FIG. 6 is a perspective view of the heat exchanger core of FIG. 4 disposed within the cylindrical shell of FIG. 5.

FIG. 5A is a perspective illustration of a cylindrical shell 62 that may be disposed within the housing 12 and arranged coaxially with the heat exchanger core 40 (see FIG. 6). FIG. 5B is a cross-sectional view of the cylindrical shell 62. The cylindrical shell 62 includes a first end 64 and a second end 66. In some embodiments, the cylindrical shell 62 may be disposed within the housing 12 such that the first end 64 is near the first end cap 14 while the second end 66 is near the second end cap 16.

The cylindrical shell 62 includes an outer surface 68. A shell aperture 70 is formed within the outer surface 68 such that blood flowing between the outer surface 52 of the heat exchanger core 40 and an inner surface 72 of the cylindrical shell 62 can exit the cylindrical shell 62. In some embodiments, the inner surface 72 of the cylindrical shell 62 may include one or more shell ribs 80 that protrude from the inner surface 72 and extend toward the heat exchanger core 40. The one or more shell ribs 80 deflect blood away from the inner surface 72 in a radially inward direction. In some embodiments, the one or more shell ribs 80 may, in combination with the core ribs 56 and 58, interrupt longitudinal blood flow and impart a radial flow component to blood flow through the heat exchanger, i.e., between the outer surface 52 of the heat exchanger core 40 and the inner surface 72 of the cylindrical shell 72. In some embodiments, the heat exchanger core 40 may also include one or more longitudinally-extending ribs 75 that may serve to promote longitudinal flow paths between the heat exchanger core 40 and the cylindrical shell 62.

In some embodiments, the cylindrical shell 62 may have one, two, three, four, five, six or any desired number of shell apertures 70 spaced radially about the cylindrical shell 62. As illustrated in FIG. 6, the core aperture(s) 54 and the shell aperture(s) 70 are generally disposed at opposite ends of the blood processing apparatus 10. Thus, blood entering the volume between the outer surface 52 of the heat exchanger core 40 and an inner surface 72 of the cylindrical shell 62 is forced to flow at least substantially the entire length thereof before exiting the cylindrical shell 62.

Figure 7:
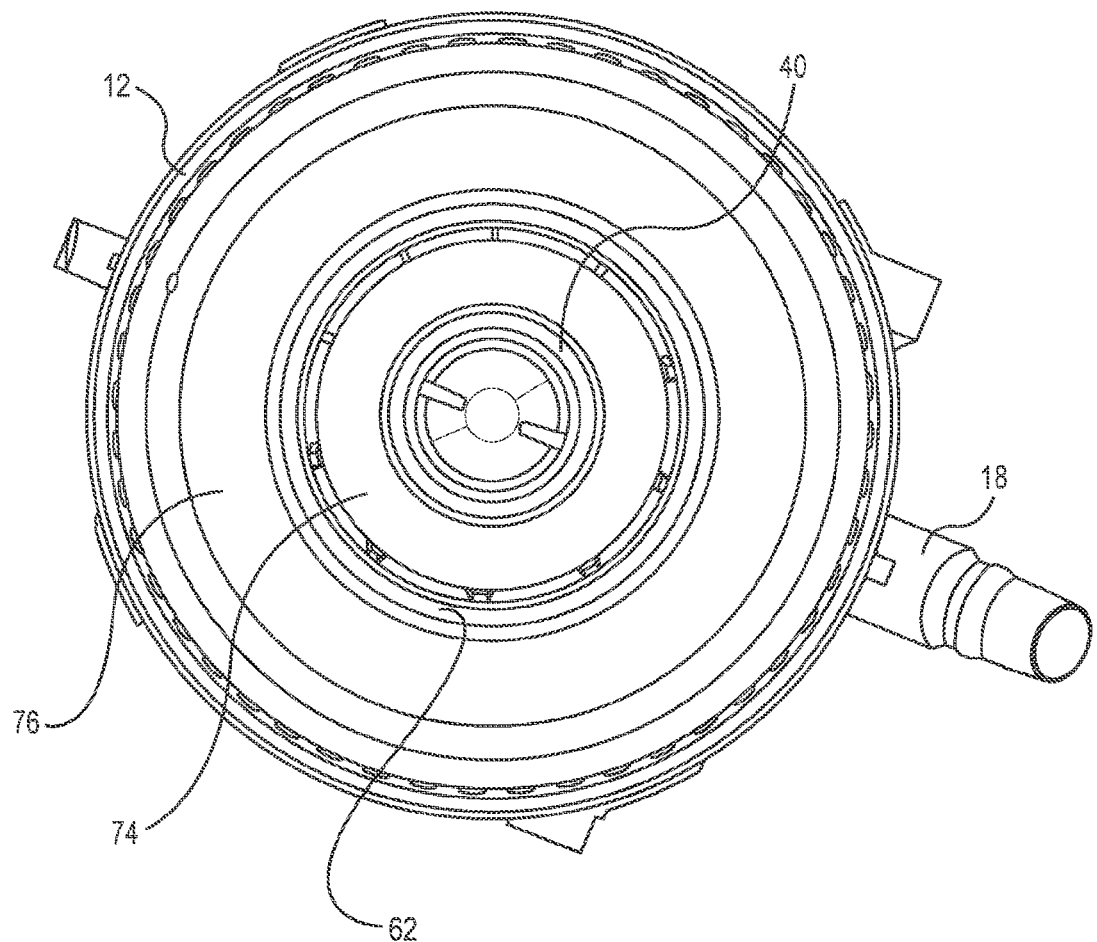
FIG. 7 is a cross-sectional view of the blood processing apparatus of FIG. 1.

FIG. 7 is a cross-sectional illustration of an embodiment of the blood processing apparatus 10, illustrating the coaxial arrangement between the housing 12, the heat exchanger core 40 and the cylindrical shell 62. In some embodiments, the blood processing apparatus 10 includes a schematically illustrated heat exchanger element 74 as well as a schematically illustrated gas exchanger element 76.

In some embodiments, the heat exchanger element 74 includes a number of hollow fibers through which a heating fluid such as water can flow. The blood may flow around and past the hollow fibers and thus be suitably heated. In some embodiments, the hollow fibers may be polymeric. In some cases, metallic fibers may be used. According to other embodiments, the heat exchanger element 74 may instead include a metal bellows or other structure having a substantial surface area (e.g., fins) for facilitating heat transfer with the blood. In some embodiments, the hollow fibers may be formed of polyurethane, polyester, or any other suitable polymer or plastic material. According to various embodiments, the hollow fibers have an outer diameter of between about 0.2 and 1.0 millimeters or, more specifically, between about 0.25 and 0.5 millimeters. The hollow fibers may be woven into mats that can range, for example, from about 80 to about 200 millimeters in width. In some embodiments, the mats are arranged in a criss-cross configuration.

In some embodiments the gas exchanger element 76 may include a number of microporous hollow fibers through which a gas such as oxygen may flow. The blood may flow around and past the hollow fibers. Due to concentration gradients, oxygen may diffuse through the microporous hollow fibers into the blood while carbon dioxide may diffuse into the hollow fibers and out of the blood. In some embodiments, the hollow fibers are made of polypropylene, polyester, or any other suitable polymer or plastic material. According to various embodiments, the hollow fibers have an outer diameter of about 0.38 millimeters. According to other embodiments, the microporous hollow fibers having a diameter of between about 0.2 and 1.0 millimeters, or more specifically, between about 0.25 and 0.5 millimeters. The hollow fibers may be woven into mats that can range, for example, from about 80 to about 200 millimeters in width. In some embodiments, the mats are in a criss-cross configuration.

Figure 8:
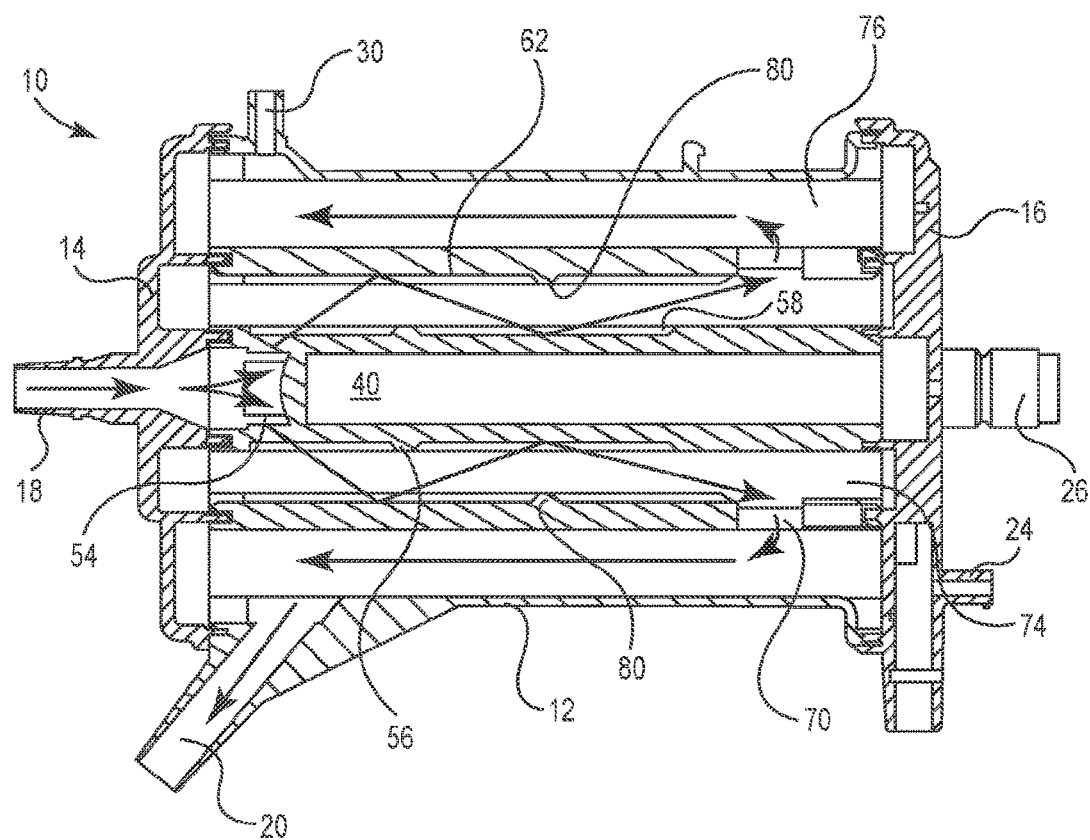
FIG. 8 is a cross-sectional illustration of a blood processing apparatus in accordance with an embodiment of the invention.

As shown in FIG. 8, blood that enters the blood processing apparatus 10 through the blood inlet 18 is radially directed through the core aperture(s) 54 such that the blood flows over and around the hollow fibers within the heat exchanger element 74. At least some of the blood flow impinges on the inner surface 72 of the cylindrical shell 62 and is radially directed back towards the outer surface 52 of the heat exchanger core 40. At least some of the blood flow is then directed radially outwards by the core ribs 56 and 58. The blood continues traveling back and forth radially until it reaches the shell aperture(s) 70 and enters a space between the cylindrical shell 62 and the housing 12. In some embodiments, improved heat transfer may be achieved by combining radial and longitudinal flow through the heat exchanger element 74. The blood exiting the shell aperture(s) 70 flows over and around the gas exchanger element 76 and eventually exits the blood processing apparatus 10 through the blood outlet 20.

FIG. 8 is a cross-sectional view of the blood processing apparatus 10, illustrating the relative orientation of the elements previously discussed. As shown, the heat exchanger core is centrally located, with the heat exchanger element 74 coaxially disposed about the heat exchanger core 40. The cylindrical shell 62 is coaxially disposed about the heat exchanger element 74, followed sequentially by the gas exchanger element 76 and the housing 12. In some embodiments, the heat exchanger core 40 may have core ribs 56 and 58 that are configured to impart a radial component to blood flow trajectory across the heat exchanger element 74. In some embodiments, the cylindrical shell 62 may have one or more radially disposed shell ribs 80 that are configured to impart a radial component to blood flow trajectory across the heat exchanger element 74.

Figure 9:
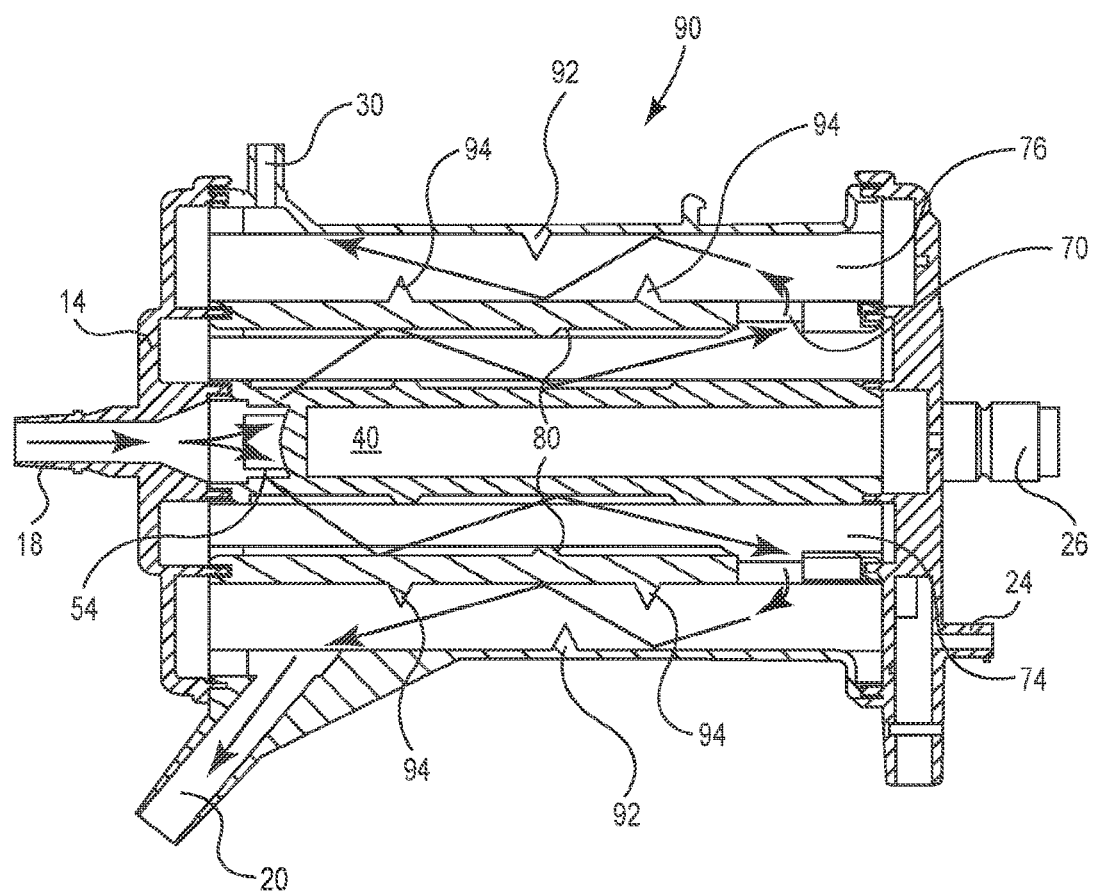
FIG. 9 is a cross-sectional illustration of a blood processing apparatus in accordance with an embodiment of the invention.

FIG. 9 is a cross-sectional view of a blood processing apparatus 90 in accordance with an embodiment of the invention. The blood processing apparatus 90 is similar to the blood processing apparatus 10, but includes a modified gas exchanger portion. In some embodiments, an inner surface of the housing 12 includes one or more housing ribs 92 that are configured to impart a radial component to blood flow trajectory through and across the gas exchanger element 76. In some embodiments, an outer surface of the cylindrical shell 62 includes one or more outer shell ribs 94 that are configured to impart a radial component to blood flow trajectory through and across the gas exchanger element 76. In some embodiments, improved gas transfer may be achieved by combining radial and longitudinal flow through the gas exchanger element 76.

In some embodiments, the ribs such as the core ribs 56 and 58, the shell ribs 80 and/or the housing ribs 92 may extend about 10 to about 70 percent of the distance between a surface from which they extend to an opposing surface. In some embodiments, the ribs may extend about 25 to about 50 percent of the aforementioned distance. To illustrate, the core ribs 56 and 58 may extend about 10 to about 70 percent, or about 25 to about 50 percent, of a distance between the heat exchanger core 40 and the cylindrical shell 62. In some embodiments, the ribs may form an angle with the surface from which they extend that is in the range of about 30 to about 90 degrees. In some embodiments, the ribs may form an angle of about 45 to about 60 degrees. In some embodiments, the ribs may have a height that is in the range of about 0.2 millimeters to about 3 millimeters and a width that is in the range of about 0.5 millimeters to about 10 millimeters.

Figure 10:
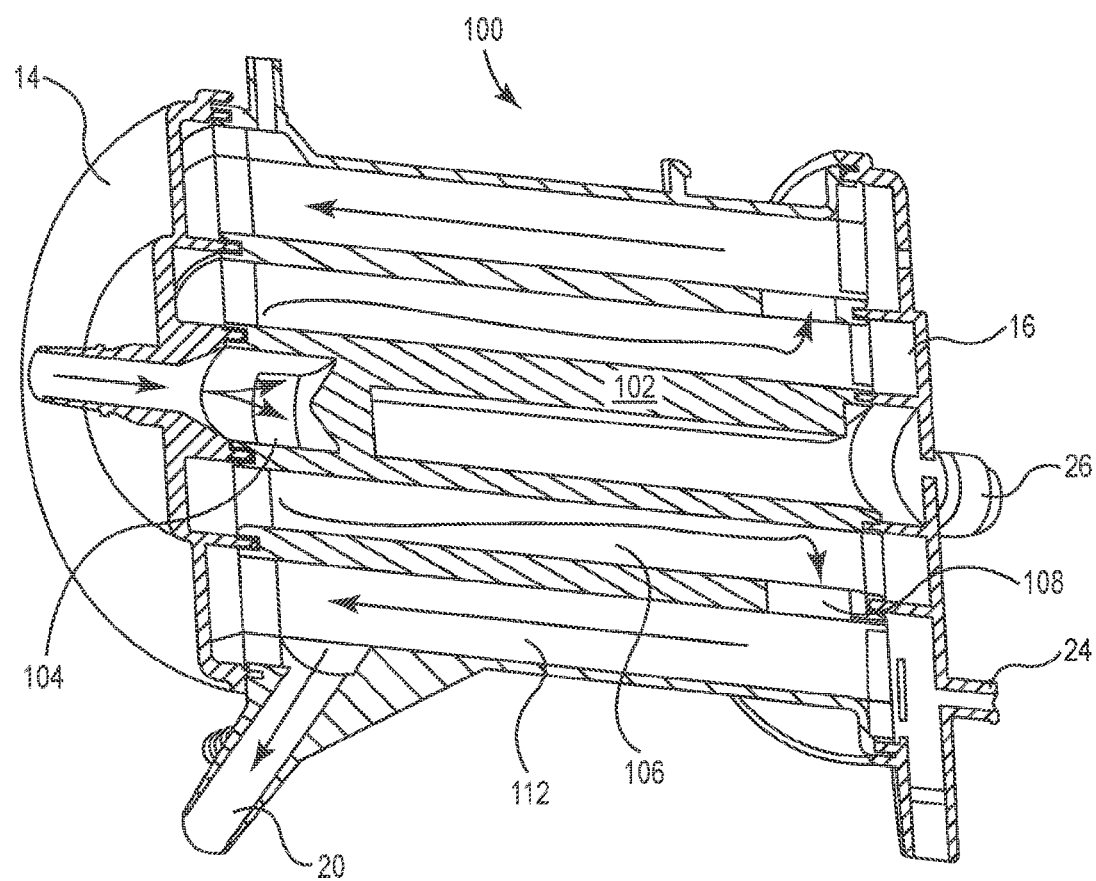
FIG. 10 is a cross-sectional illustration of a blood processing apparatus in accordance with an embodiment of the invention.

FIG. 10 is a cross-sectional view of a blood processing apparatus 100 in accordance with an embodiment of the invention. The blood processing apparatus 100 is similar to those discussed above, but blood flow through the heat exchanger has a spiral component. The blood processing apparatus 100 has a heat exchanger core 102 that includes one or more core apertures 104. Blood passes through the one or more core apertures 104 and enters a heat exchanger element 106 that as discussed above may include a number of hollow fibers. Blood exits the heat exchanger element 106 through one or more shell apertures 108 and then passes longitudinally through a gas exchanger element 112 before exiting through the blood outlet 20.

Figure 11:
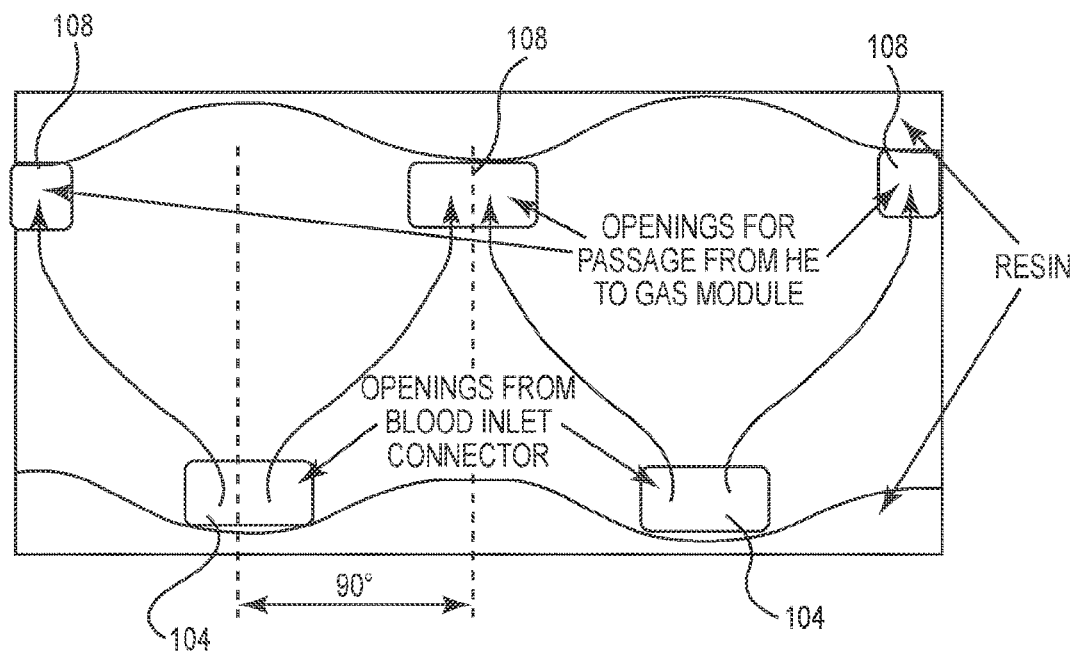
FIG. 11 is a diagram illustrating blood flow paths in the blood processing apparatus of FIG. 10.

As shown in FIG. 10 that the core apertures 104 and the shell apertures 108 are longitudinally spaced apart such that blood entering the heat exchanger element 106 passes the length of the heat exchanger element 106 before exiting into the gas exchanger element 112. The core apertures 104 and the shell apertures 108 are radially spaced apart from one another. As schematically shown in FIG. 11, for example, the core apertures 104 may be spaced about 180 degrees apart from each other. The shell apertures 108 may also be spaced about 180 degrees apart from each other, and moreover may be radially displaced from the core apertures 104 by about 180 degrees. As a result, blood passing through the heat exchanger element 106 undergoes a spiral flow path through and around the hollow fibers within the heat exchanger element 106.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A blood processing apparatus comprising:
   a housing having a blood inlet and a blood outlet, the blood inlet extending into an interior of the housing;
   a heat exchanger core arranged within the housing, the heat exchanger core having one or more core ribs protruding from an outer surface of the heat exchanger core;
   a shell extending around the heat exchanger core and defining a first space between the outer surface of the heat exchanger core and an inner surface of the shell, the shell having one or more shell ribs protruding from the inner surface of the shell toward the heat exchanger core;
   heat exchanger hollow fibers disposed in the first space between the heat exchanger core and the shell such that a heat exchanger fluid may flow through the heat exchanger hollow fibers and blood passing through the first space may flow across the heat exchanger hollow fibers; and
   gas exchanger hollow fibers disposed around the shell such that gas may flow through the gas exchanger hollow fibers and blood passing from the shell aperture may flow across the gas exchanger hollow fibers;
   wherein the one or more core ribs and the one or more shell ribs are each configured to radially deflect blood flow such that blood passing from the blood inlet and along the outer surface of the heat exchanger core is radially deflected by the one or more core ribs through the heat exchanger hollow fibers toward the inner surface of the shell and at least some of the blood is radially deflected by the one or more shell ribs back toward the outer surface of the heat exchanger core.

2. The blood processing apparatus of claim 1, wherein the heat exchanger core includes one or more longitudinal core ribs configured to promote longitudinal flow of blood down the outer surface of the heat exchanger core.

3. The blood processing apparatus of claim 1, wherein the shell includes one or more longitudinally disposed shell ribs extending from the inner surface of the shell toward the heat exchanger core to promote longitudinal blood flow along the inner surface of the shell.

4. The blood processing apparatus of claim 1, wherein the housing includes an inner surface upon which one or more housing ribs are disposed, the one or more housing ribs configured to impart a radial component to blood flow trajectory across the gas exchanger hollow fibers.

5. The blood processing apparatus of claim 1, wherein the shell includes one or more shell apertures disposed near a second end of the housing such that blood passing back and forth radially through the first space between the heat exchanger core and the shell flows through the one or more shell apertures into a second space between the shell and the housing.

6. The blood processing apparatus of claim 5, wherein the heat exchanger core includes a core aperture disposed near a first end of the housing.

7. The blood processing apparatus of claim 6, wherein the heat exchanger core includes a conical deflection surface disposed between the blood inlet and the core aperture, the conical deflection surface imparting a radial component to blood flow trajectory leaving the core aperture.

8. The blood processing apparatus of claim 7, wherein the conical deflection surface includes a divider that assists in directing blood in particular directions.

9. The blood processing apparatus of claim 6, wherein the core aperture comprises a pair of core apertures disposed about 180 degrees apart, and the shell aperture comprises a pair of shell apertures that are disposed about 180 degrees apart and radially offset from the pair of core apertures in order to alter blood flow trajectory of the blood flowing across the heat exchanger hollow fibers.

10. The blood processing apparatus of claim 1, further comprising a first end cap secured to the housing, the blood inlet being integrally formed with the first end cap.

11. The blood processing apparatus of claim 10, further comprising a gas inlet integrally formed with the first end cap, the gas inlet in fluid communication with an interior of the gas exchanger hollow fibers.

12. The blood processing apparatus of claim 10, further comprising a second end cap secured to the housing, the second end cap including a heat exchanger fluid inlet integrally formed with the second end cap and a heat exchanger fluid outlet integrally formed with the second end cap, the heat exchanger fluid inlet and outlet each in fluid communication with an interior of the heat exchanger hollow fibers.

13. A blood processing apparatus comprising:
a housing having a blood inlet and a blood outlet, the blood inlet extending into an interior of the housing;
a heat exchanger core arranged within the housing and having a core aperture in fluid communication with the blood inlet and an outer surface of the heat exchanger core;
a shell extending around the heat exchanger core and defining a first space between the outer surface of the heat exchanger core and an inner surface of the shell, the shell having at least one shell aperture disposed near a second end of the housing such that blood passing from the core aperture may flow through the first space to the shell aperture imparting a longitudinal blood flow component to the blood;
heat exchanger hollow fibers disposed around the heat exchanger core in the first space such that a heat exchanger fluid may flow through the heat exchanger hollow fibers and blood passing through the first space may flow across the heat exchanger hollow fibers;
gas exchanger hollow fibers disposed around the shell such that gas may flow through the gas exchanger hollow fibers and blood passing from the shell aperture may flow across the gas exchanger hollow fibers;
wherein the shell includes at least one protrusion extending into the first space, the at least one protrusion configured to impart a radial flow component to the blood to deflect the blood toward the outer surface of the heat exchanger core from the inner surface of the shell as the blood passes from the core aperture to the shell aperture.

14. The blood processing apparatus of claim 13, further comprising one or more radially disposed core ribs protruding from the outer surface of the heat exchanger core toward the shell.

15. The blood processing apparatus of claim 13, wherein the at least one protrusion includes one or more circumferential shell ribs protruding from the inner surface of the shell toward the heat exchanger core.

16. The blood processing apparatus of claim 13, wherein the heat exchanger core includes one or more longitudinal core ribs configured to promote longitudinal flow of blood down the outer surface of the heat exchanger core.

17. The blood processing apparatus of claim 13, wherein the shell includes one or more longitudinally disposed shell ribs extending from the inner surface of the shell toward the heat exchanger core to promote longitudinal blood flow along the inner surface of the shell.

18. The blood processing apparatus of claim 13, further comprising a second space between an outer surface of the shell and an inner surface of the housing, wherein at least one of the housing and the shell includes at least one rib extending into the second space, the at least one rib configured to impart a radial flow component to the blood to deflect the blood toward the outer surface of the shell from the inner surface of the housing and/or toward the inner surface of the housing from the outer surface of the shell as the blood passes through the second space.

19. A blood processing apparatus comprising:
a housing having a first end, a second end opposite the first end, a blood inlet and a blood outlet, the blood inlet extending into an interior of the housing;
a heat exchanger core arranged within the housing and having and an outer surface;
a shell extending around the heat exchanger core and defining a first space between the outer surface of the heat exchanger core and an inner surface of the shell, and a second space between an outer surface of the shell and an inner surface of the housing;
heat exchanger hollow fibers disposed around the heat exchanger core in the first space such that a heat exchanger fluid may flow through the heat exchanger hollow fibers and blood passing through the first space may flow across the heat exchanger hollow fibers;
gas exchanger hollow fibers disposed around the shell in the second space such that gas may flow through the gas exchanger hollow fibers and blood may flow across the gas exchanger hollow fibers;
wherein the shell includes at least one rib extending into the first space, the at least one rib configured to impart a radial flow component to the blood to deflect the blood toward the outer surface of the heat exchanger core from the inner surface of the shell as the blood passes through the first space.

20. The blood processing apparatus of claim 19, wherein at least one of the housing and the shell includes at least one rib extending into the second space, the at least one rib configured to impart a radial flow component to the blood to deflect the blood toward the outer surface of the shell from the inner surface of the housing and/or toward the inner surface of the housing from the outer surface of the shell as the blood passes through the second space.

* * * * *